United States Patent [19]

Yount et al.

[11] Patent Number: 5,082,982
[45] Date of Patent: Jan. 21, 1992

[54] OXYIODINATION PROCESS FOR MANUFACTURE OF 2,6-DIIODONAPHTHALENE

[75] Inventors: Thomas L. Yount, Mt. Carmel; George G. Mayfield; Victor H. Agreda, both of Kingsport, all of Tenn.

[73] Assignee: Eastman Kodak Company, Rochester, N.Y.

[21] Appl. No.: 608,423

[22] Filed: Nov. 2, 1990

[51] Int. Cl.$^5$ ............................................. C07C 17/152
[52] U.S. Cl. .................................................... 570/203
[58] Field of Search ......................................... 570/203

[56] References Cited

U.S. PATENT DOCUMENTS 4,746,758  5/1988  Rule et al. ............................ 570/206
4,788,356  11/1988  Tustin .................................... 570/203

Primary Examiner—Howard T. Mars
Assistant Examiner—Kimberly J. Kestler
Attorney, Agent, or Firm—Charles R. Martin; William P. Heath, Jr.

[57] ABSTRACT

Disclosed is a process for preparation of a stream which is both selectively high in 2,6-diiodonaphthalene and also contains substantial quantities of diiodonaphthalene. First, naphthalene is oxyiodinated in the presence of a zeolite catalyst to produce a stream which is selectively high in 2-monoiodonaphthalene and the 2-monoiodonaphthalene is separated from the stream to produce a stream which is both selectively high in 2-monoiodonaphthalene and contains substantial quantities of 2-monoiodonaphthalene. Second, this stream is then oxyiodinated in the presence of a zeolite catalyst to produce a stream which is selectively high in 2,6-diiodonaphthalene and then 2,6-diiodonaphthalene is separated from the stream to produce the stream which is both selectively high in 2,6-diiodonaphthalene and contains substantial quantities of 2,6-diiodonaphthalene.

1 Claim, 1 Drawing Sheet

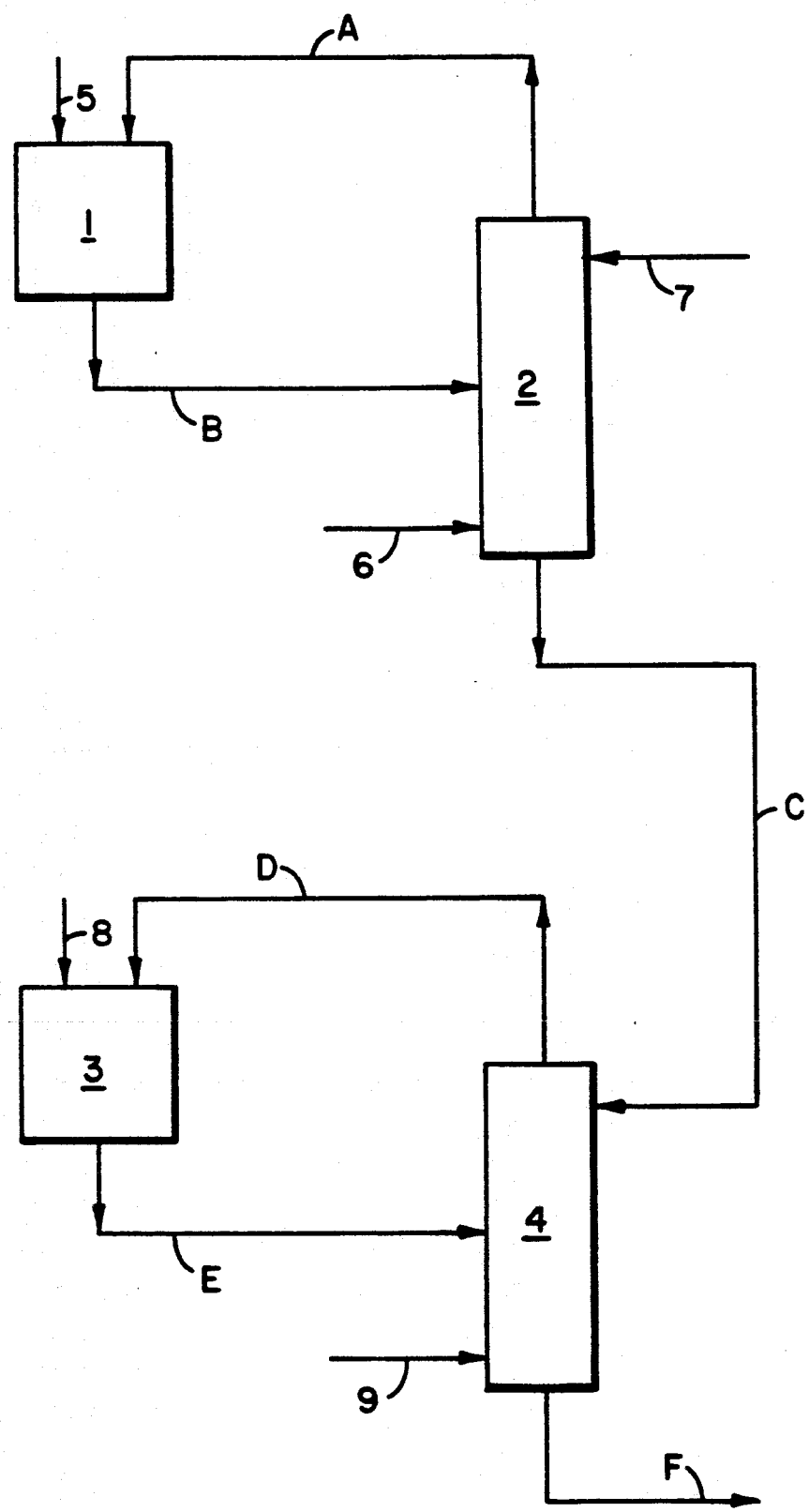
Figure

OXYIODINATION PROCESS FOR MANUFACTURE OF 2,6-DIIODONAPHTHALENE

This invention relates to the manufacture of 2,6-diiodonaphthalene.

The compound 2,6-dimethyl naphthalene dicarboxylate is a particularly desirable material for use in the manufacture of polyesters which have excellent barrier properties in packaging applications.

This compound can be prepared using a number of different methods, including the carboxylation of 2,6-diiodonaphthalene. The compound 2,6-diiodonaphthalene in turn can be prepared in a variety of ways, including reacting naphthalene with oxygen and iodine in the presence of a zeolite catalyst in accordance with U.S. Pat. No. 4,746,758.

Although this oxyiodination method for preparation of 2,6-diiodonaphthalene has many desirable features, the yield of 2,6-diiodonaphthalene many other unwanted iodonaphthalene compounds are also produced, such as 1-monoiodonaphthalene, 2,7-diiodonaphthalene, 2,5-diiodonaphthalene, triiodonaphthalenes and tetraiodonaphthalenes.

Research has shown that the oxyiodination reaction described in U.S. Pat. No. 4,746,758 has several highly selective aspects. One aspect is that the amount of 2,6-diiodonaphthalene produced is selectively low and also low in yield. The amount of 2-monoiodonaphthalene produced is selectively high but low in yield. Research has further shown that the amount of 2,6-diiodonaphthalene which is produced depends in large measure on the materials fed to the oxyiodination reaction. For example, oxyiodination of naphthalene and 2-monoiodonaphthalene tends to form the desired 2,6-diiodonaphthalene more so than oxyiodination of other iodonaphthalenes such as 1-monoiodonaphthalene, which leads to the formation of undesired iodonaphthalenes. Thus, the greater the amount of 2-monoiodonaphthalene and naphthalene which is contained in a stream to be oxyiodinated the greater the amount of 2,6-diiodonaphthalene that will be produced.

In summary, this process can be thought of as a process composed of two basic steps.

In the first step, naphthalene is oxyiodinated to produce a stream which is selectively high in 2-monoiodonaphthalene but is low in amount of 2-monoiodonaphthalene. The 2-monoiodonaphthalene is then separated from this stream to produce a stream which is both selectively high in 2-monoiodonaphthalene and contains substantial quantities of 2-monoiodonaphthalene. As a result of the first step the balance of mixed iodonaphthalenes is shifted so as to substantially increase the amount of 2-monoiodonaphthalene.

In the second step, the stream from the first step is then oxyiodinated to produce a stream which is selectively high in 2,6-diiodonaphthalene but low in amount of 2,6-diiodonaphthalene. The 2,6-diiodonaphthalene is then separated from this stream to produce the product stream which is both selectively high in 2,6-diiodonaphthalene and also contains substantial quantities of 2,6-diiodonaphthalene. As a result of the second step the balance of mixed iodonaphthalenes is shifted so as to substantially increase the amount of 2,6-diiodonaphthalene.

Broadly the process of this invention can be described as a process comprising (A) selectively preparing 2-monoiodonaphthalene within a first zone comprised of a first oxyiodination sub-zone and a first separation sub-zone by
  (1) introducing into the first oxyiodination sub-zone iodine and an oxygen and naphthalene containing stream which is withdrawn from the first separation zone,
  (2) selectively oxyiodinating within the first oxyiodination sub-zone in the presence of an X type zeolite catalyst a portion of the naphthalene in the oxygen and naphthalene containing stream into 2-monoiodonaphthalene,
  (3) withdrawing from the first oxyiodination sub-zone a stream which is selectively high in 2-monoiodonaphthalene relative to 1-monoiodonaphthalene,
  (4) introducing the stream which is withdrawn from the first oxyiodination sub-zone and is selectively high in 2-monoiodonaphthalene relative to 1-monoiodonaphthalene into the first separation sub-zone,
  (5) introducing oxygen into the first separation sub-zone,
  (6) introducing naphthalene into the first separation sub-zone,
  (7) separating within the first separation sub-zone the stream which is selectively high in 2-monoiodonaphthalene relative to 1-monoiodonaphthalene into a stream which is selectively high in 2-monoiodonaphthalene relative to all other iodonaphthalenes,
  (8) withdrawing from the first separation sub-zone the stream which is selectively high in 2-monoiodonaphthalene relative to other iodonaphthalenes,
(B) selectively preparing 2,6-diiodonaphthalene within a second zone comprised of a second oxyiodination sub-zone and a second separation sub-zone by
  (1) introducing into the second oxyiodination sub-zone iodine and a stream which is withdrawn from the second separation sub-zone and is selectively high in 2-monoiodonaphthalene and contains oxygen,
  (2) selectively oxyiodinating within the second oxyiodination sub-zone in the presence of an X type zeolite catalyst the 2-monoiodonaphthalene in the stream which is selectively high in 2-monoiodonaphthalene and contains oxygen into 2,6-diiodonaphthalene,
  (3) withdrawing from the second oxyiodination sub-zone a stream which is selectively high in 2,6-diiodonaphthalene relative to other naphthalenes,
  (4) introducing into the second separation sub-zone the stream which is withdrawn from the second oxyiodination sub-zone and is selectively high in 2,6-diiodonaphthalene relative to other diiodonaphthalenes,
  (5) introducing into the second separation sub-zone the stream which is withdrawn from the first separation sub-zone and is both selectively high in 2-monoiodonaphthalene and contains substantial quantities of 2-monoiodonaphthalene,
  (6) introducing oxygen into the second separation sub-zone,
  (7) separating within the second separation sub-zone the stream which is selectively high in 2,6-diiodonaphthalene into a stream which is selectively high in 2,6-diiodonaphthalene relative to other iodonaphthalenes,
  (8) withdrawing from the second separation sub-zone the stream which is selectively high in 2,6-diiodonaphthalene relative to all other iodonaphthalenes.

In a preferred embodiment of the invention, the product stream which is both selectively high in 2,6-diiodonaphthalene and contains substantial quantities of 2,6-diiodonaphthalene is introduced into a crystallizer wherein the 2,6-diiodonaphthalene is recovered by crystallization and the remaining stream which contains substantial quantities of mixed iodinated naphthalenes is introduced into a hydrodehalogenation reactor wherein a substantial amount of the mixed iodinated naphthalenes are restructured into iodine and naphthalene and an iodine rich stream and a naphthalene rich stream are withdrawn from the hydrodehalogenation reactor. The iodine rich stream from the hydrodehalogenation reactor is then combined with make up iodine to form the iodine stream which is introduced into both the first and second oxyiodination sub-zones. Similarly, the naphthalene rich stream which is withdrawn from the hydrodehalogenation reactor is combined with makeup naphthalene to form the naphthalene containing stream which is introduced into the first separation sub-zone.

This process can be more completely understood by a consideration of the following specific embodiment which is described in the attached Figure and below Table which shows the mole percentage of the compounds of the streams designated by alphabetical letters in the Figure.

In summary, the process illustrated schematically in the Figure involves introducing oxygen, naphthalene and iodine into first oxyiodination reactor 1 and a first separation means 2 which produces stream C which is selectively high in 2-monoiodonaphthalene and also contains substantial quantities of 2-monoiodonaphthalene. This stream is then introduced into a second oxyiodination reactor 3 and a second separation means 4 along with oxygen and iodine to produce product stream F which is both selectively high in 2,6-diiodonaphthalene and also contains substantial quantities of 2,6-diiodonaphthalene.

TABLE

| Component | Stream |  |  |  |  |  |
|---|---|---|---|---|---|---|
|  | A | B | C | D | E | F |
| 2-monoiodonaphthalene | 0.16 | 1.73 | 73.8 | 12.5 | 11.6 | 4.9 |
| 1-monoiodonaphthalene | 0.03 | 0.34 | 14.7 | 2.8 | 2.6 | 0.9 |
| 2,6-diiodonaphthalene | 0 | 0.03 | 1.25 | 0.006 | 0.9 | 64.3 |
| 2,7-diiodonaphthalene | 0 | 0.006 | 0.31 | 0.002 | 0.18 | 12.9 |
| Naphthalene | 26.5 | 23.9 | 9.5 | 0.6 | 0.5 | 0.02 |
| Other | 73.3 | 73.0 | 0.35 | 84.1 | 84.2 | 17.0 |

Referring to the Figure, a stream of iodine 5 is introduced into a first oxyiodination reactor 1 along with oxygen and naphthalene containing stream A which is withdrawn from first separation means 2. Stream 5 can be entirely makeup iodine but in a preferred embodiment stream 5 is a combination of makeup iodine and the iodine rich stream withdrawn from the hydrodehalogenation reactor.

As will be noted from the material balance in the Table, stream A is composed of naphthalene and other materials such as nitrogen, oxygen, carbon dioxide, water and mixed iodonaphthalenes.

Within oxyiodinated reactor 1 a portion of the naphthalene in oxygen and naphthalene containing stream A is selectively oxyiodinated into 2-monoiodonaphthalene to form stream B which is withdrawn from first oxyiodination reactor 1.

The oxyiodination reaction occurring within reactor 1 is well known in the art and is disclosed in U.S. Pat. No. 4,746,758, here incorporated by reference. In summary, in this process oxygen, iodine and naphthalene are contacted in the presence of an X type zeolite catalyst which preferably contains a counter ion such as potassium or sodium. The preferred zeolite is a 13X type which contains potassium as the counter ion.

As noted in the Table, the amount of 2-monoiodonaphthalene in stream B is not large in comparison to the entire stream but is large in comparison to the amount of 1-monoiodonaphthalene, 2,6-diiodonaphthalene and 2,7-diiodonaphthalene.

Stream B which is withdrawn from first oxyiodination reactor 1 is introduced into first separation means 2 along with a stream of oxygen 6 and a stream of naphthalene 7. Preferably, stream 7 is composed of makeup naphthalene and the naphthalene-rich stream from the hydrodehalogenation reactor.

Separation means 2 is a conventional separation means well known in the art such as distillation or gas stripping. Preferably the separation means is gas stripping.

As a result of the separation occurring within first separation means 2 stream A is returned to oxyiodinated reactor 1 and stream C is withdrawn. As will be noted from the Table, Stream C is both selectively high in 2-monoiodonaphthalene and also contains substantial quantities of 2-monoiodonaphthalene.

In accordance with this invention stream C is then used to prepare a stream which is both selectively high in 2,6-diiodonaphthalene and also contains substantial quantities of 2,6-diiodonaphthalene.

Stream 8 containing iodine is introduced into second oxyiodination reactor 3. This stream can be composed entirely of makeup iodine or preferably can be the combination of the iodine rich stream from the hydrodehalogenation reactor and makeup iodine.

Stream D which is withdrawn from second separation means 4 and is selectively high in 2-monoiodonaphthalene and contains oxygen is also introduced into oxyiodination reactor 3.

The oxyiodination reaction occurring within oxyiodinated reactor 3 is also disclosed in U.S Pat. No. 4,746,258.

Within oxyiodination reactor 3 the 2-monoiodonaphthalene in stream D is oxyiodinated into 2,6-diiodonaphthalene to form stream E which as shown in the Table is selectively high in 2,6-diiodonaphthalene but does not contain substantial quantities of 2,6-diiodonaphthalene.

Stream E is then introduced into second separation means 4 along with a stream of oxygen 9. As a result of the separation within separation means 4 there is produced previously described stream D which is recycled to oxyiodination reactor 2 as well as product stream F. As will be noted from the Table, stream F is both selectively high in 2,6-diiodonaphthalene and also contains substantial quantities of 2,6-diiodonaphthalene.

Separation means 4 can be a conventional separation means such as described for separation means 2. Preferably separation means 4 is gas stripping.

We claim:
1. A process comprising
   (A) selectively preparing 2-monoiodonaphthalene within a first zone comprised of a first oxyiodination sub-zone and a first separation sub-zone by
      (1) introducing into the first oxyiodination sub-zone iodine and an oxygen and naphthalene containing stream which is withdrawn from the first separation zone,
      (2) selectively oxyiodinating within the first oxyiodination sub-zone in the presence of an 13X zeolite catalyst a portion of the naphthalene in the oxygen and naphthalene containing stream into 2-monoiodonaphthalene, (3) withdrawing from the first oxyiodination sub-zone a stream which is selectively high in 2-monoiodonaphthalene, (4) introducing the stream which is withdrawn from the first oxyiodination sub-zone and is selectively high in 2-monoiodonaphthalene into the first separation sub-zone, (5) introducing oxygen into the first separation sub-zone, (6) introducing naphthalene into the first separation sub-zone, (7) separating within the first separation sub-zone the stream which is selectively high in 2-monoiodonaphthalene into a stream which is both selectively high in 2-monoiodonaphthalene and contains substantial quantities of 2-monoiodonaphthalene, (8) withdrawing from the first separation sub-zone the stream which is both selectively high in 2-monoiodonaphthalene and contains substantial quantities of 2-monoiodonaphthalene, (B) selectively preparing 2,6-diiodonaphthalene within a second zone comprised of a second oxyiodination sub-zone and a second separation sub-zone by (1) introducing into the second oxyiodination sub-zone iodine and a stream which is withdrawn from the second separation sub-zone and is selectively high in 2-monoiodonaphthalene and contains oxygen, (2) selectively oxyiodinating within the second oxyiodination sub-zone in the presence of an 13X zeolite catalyst the 2-monoiodonaphthalene in the stream which is selectively high in 2-monoiodonaphthalene and contains oxygen into 2,6-diiodonaphthalene, (3) withdrawing from the second oxyiodination sub-zone a stream which is selectively high in 2,6-diiodonaphthalene, (4) introducing into the second separation sub-zone the stream which is withdrawn from the second oxyiodination sub-zone and is selectively high in 2,6-diiodonaphthalene, (5) introducing into the second separation sub-zone the stream which is withdrawn from the first separation sub-zone and is selectively high in 2-monoiodonaphthalene, (6) introducing oxygen into the second separation sub-zone, (7) separating within the second separation sub-zone the stream which is selectively high in 2,6-diiodonaphthalene into a stream which is both selectively high in 2,6-diiodonaphthalene and contains substantial quantities of 2,6-diiodonaphthalene, (8) withdrawing from the second separation sub-zone the stream which is both selectively high in 2,6-diiodonaphthalene and contains substantial quantities of diiodonaphthalene.

* * * * *